United States Patent [19]

Barder

[11] Patent Number: 4,882,065

[45] Date of Patent: * Nov. 21, 1989

[54] PURIFICATION OF STEROLS WITH ACTIVATED CARBON AS ADSORBENT AND CHLOROBENZENE AS DESORBENT

[75] Inventor: Timothy J. Barder, Addison, Ill.

[73] Assignee: UOP, Des Plaines, Ill.

[*] Notice: The portion of the term of this patent subsequent to Jul. 18, 2006 has been disclaimed.

[21] Appl. No.: 131,611

[22] Filed: Dec. 11, 1987

[51] Int. Cl.$^4$ ............................................. B01D 15/00
[52] U.S. Cl. .................... 210/674; 210/694; 260/397.25
[58] Field of Search ............... 210/674, 690, 691, 694; 260/397.25

[56] References Cited

U.S. PATENT DOCUMENTS

| | | | |
|---|---|---|---|
| 2,985,589 | 5/1961 | Broughton | 210/34 |
| 3,040,777 | 6/1962 | Carson et al. | 137/625.15 |
| 3,422,848 | 1/1969 | Liebman et al. | 137/625.15 |
| 3,706,812 | 12/1972 | DeRosset et al. | 260/674 SA |
| 4,664,807 | 5/1987 | Van Dam et al. | 210/635 |

OTHER PUBLICATIONS

W. J. Dorson et al., Trans. Am. Soc. Artif. Intern. Organs, 25, pp. 77–80, 1979.

Primary Examiner—Ivars Cintins
Attorney, Agent, or Firm—Thomas K. McBride; John F. Spears, Jr.; Jack H. Hall

[57] ABSTRACT

An adsorptive separation process for separating sterols from a tall oil feed mixture, which process comprises contacting the feed mixture with an adsorbent comprising an activated-type carbon sieve having a pore diameter of 15–20 Å and a surface area of 300–1500 m$^2$/g, selectively adsorbing substantially all of the sterols to be separated on the adsorbent and thereafter recovering high purity sterols. A desorption step is used to desorb the adsorbed sterols with an aromatic liquid, e.g., chlorobenzene.

14 Claims, 2 Drawing Sheets

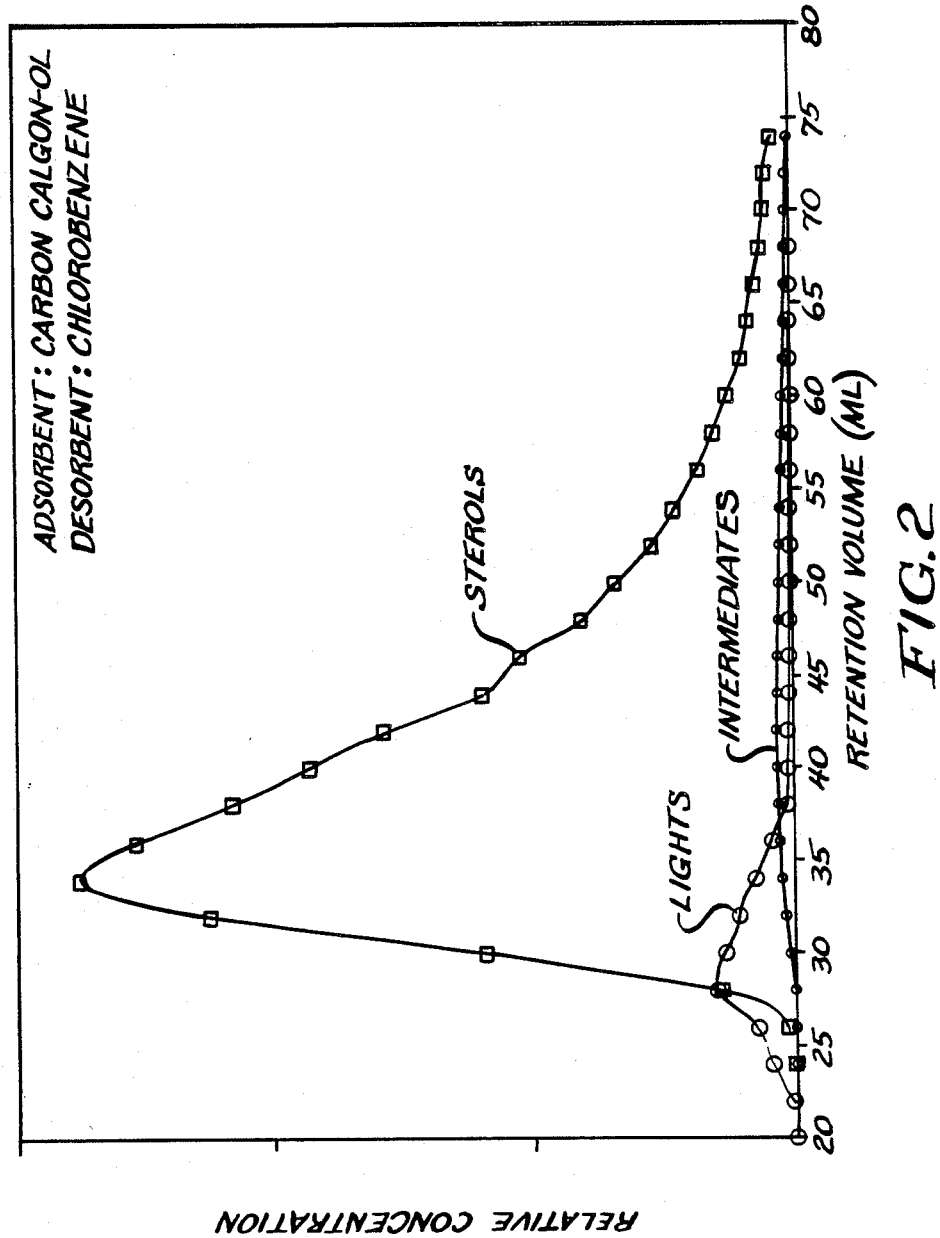

PURIFICATION OF STEROLS WITH ACTIVATED CARBON AS ADSORBENT AND CHLOROBENZENE AS DESORBENT

BACKGROUND OF THE INVENTION

1. Field of the Invention

The field of art to which the invention pertains is solidbed adsorptive separation. Specifically, it relates to an improved process for separating sterols from sterol-containing material found occurring in nature. The improved process utilizes an adsorbent and desorbent particularly adapted, in combination, to separate the sterols without deactivating the adsorbent.

2. Description of the Prior Art

It is known in the art to separate sterols from tall oil fractions, e.g., pitch, and cholesterol from wool fat, etc. U.S. Pat. No. 4,664,807 discloses the method of isolating cholesterol from a source of sterol-containing material in a column packed with alumina, magnesium silicate (Florisil) or silica gel and eluting the cholesterol with a liquid such as heptane-acetone 19:1 (v:v), toluene; acetone 29:1 (v:v), toluene heptane-n-butyl acetate 5:1 (v:v) or heptane-toluene-acetone 70:1:9. However, the acids in tall oil will rapidly deactivate the Florisil and silica adsorbents.

Tall oil contains several sterols, e.g., $\alpha$-and $\beta$-sitosterol, the latter of which is especially used in cosmetics, such as moisturizing cream, lipstick, etc., as an emulsifier, viscosity regulator, emulsion stabilizer and skin softener. Phytosterol was separated from sulfate soap, a by-product of tall oil manufacture, by column chromatography on alumina by the Russians, Nekrasova and Kaganovich and Associates. Cholesterol has been adsorbed onto activated charcoal and steady state reached by W. S. Dorson et al., Trans, Am. Soc., Artif., Intern. Organs, 25, pp 77-80, 1979.

SUMMARY OF THE INVENTION

It is an object of the present invention to separate sterols from the sterol-containing natural material, thereby obtaining said sterols in more concentrated form and/or with greater purity. Sterols, such as sitosterol and cholesterol, are naturally occurring and of great importance because of their usefulness in synthesizing valuable substances such as vitamins, hormones and other pharmaceutical products. The process by which they are recovered must be technically capable of recovering the sterol in sufficient purity and yield and economical enough to satisfy commercial demands.

In brief summary, the invention is a process for separating sterols from a feed containing sterols and other materials, for example, tall oil, which contain $\beta$-sitosterol and other sterols plus undesirables: di- and triterpene alcohols, fatty alcohols, diterpene aldehydes, squalene and polymeric materials, or wool fats, containing cholesterol. The process comprises contacting at adsorption conditions, said feed, with an adsorbent comprising an activated-type carbon sieve having a pore diameter (calculated from the formula $$\frac{4 \times \text{volume}}{\text{S.A. (Langmuir)}}$$

in the range of 15-20 angstroms (Å) and a Langmuir surface area of 400-1500 m²/g, selectively adsorbing the sterols to the substantial exclusion of the alcohols, aldehydes, and polymers present and thereafter recovering high-purity , $\beta$-sitosterol or cholesterol by desorbing said carbon with a desorbent material such as chlorobenzene at desorption conditions. Furthermore, the more hydrophilic adsorbents, alumina, silica and magnesium silicate (Florisil) are not as stable to the acid impurities as the carbons of the invention. For example, in a continuous countercurrent, simulated moving bed adsorptive separation, such as that disclosed in Broughton U.S. Pat. No. 2,985,589, referred to in more detail hereinafter, deactivation of Florisil takes place even at the low level of 2% of resin acids present, whereas the carbons of the present invention have been observed free of deactivation after 10 bed volumes of feed have been passed over the adsorbent.

In another embodiment, the present invention is a process for separating sterols from a feed mixture comprising said sterols and impurities including terpene alcohols, fatty alcohols, diterpene aldehydes and polymeric materials, which process comprises contacting at adsorption conditions the mixture with an adsorbent comprising an activated carbon with the above properties, which process comprises the steps of: (a) maintaining net fluid flow through a column of the adsorbent in a single direction, which column contains at least three zones having separate operational functions occurring therein and being serially interconnected with the terminal zones of the column connected to provide a continuous connection of the zones; (b) maintaining an adsorption zone in the column, the zone defined by the adsorbent located between a feed inlet stream at an upstream boundary of the zone and a raffinate outlet stream at a downstream boundary of the zone; (c) maintaining a purification zone immediately upstream from the adsorption zone, the purification zone defined by the adsorbent located between an extract outlet stream at an upstream boundary of the purification zone and the feed inlet stream at a downstream boundary of the purification zone; (d) maintaining a desorption zone immediately upstream from the purification zone, the desorption zone defined by the adsorbent located between a desorbent inlet stream at an upstream boundary of the zone and the extract outlet stream at a downstream boundary of the zone; (e) passing the feed stream into the adsorption zone at adsorption conditions to effect the selective adsorption of he sterol by the adsorbent in the adsorption zone and withdrawing a raffinate outlet stream from the adsorption zone; (f) passing chlorobenzene into the desorption zone at desorption conditions to effect the displacement of the sterol from the adsorbent in the desorption zone; (g) withdrawing an extract stream comprising the sterol and desorbent material from the desorption zone; and (h) periodically advancing through the column of adsorbent in a downstream direction with respect to fluid flow in the adsorption zone, the feed inlet stream, raffinate outlet stream, desorbent inlet stream, and extract outlet stream to effect the shifting of zones through the adsorbent and the production of extract outlet and raffinate outlet streams.

In this embodiment, the invention is realized through the employment of an adsorbent of activated carbon to adsorb the sterol components mentioned above and chlorobenzene as desorbent to desorb the sterol fraction from the carbon. Activated carbon, as used as an adsorbent in the present invention, is the commonly known, stable, amorphous form of carbon derived from a naturally-occurring material, such as set forth below, which has been treated with steam to obtain a large surface area. The large surface area implies there exists a highly developed internal pore structure in the activated carbon, thus providing the well-known ability to adsorb gases and vapors and various substances dissolved or dispersed in liquids. Activated carbon used for liquid phase operations, such as decolorizing, is normally a light fluffy powder, while that used for gas phase operations, such as vapor adsorption, is usually a hard, dense granular pellet. The former is commonly derived from bones, wood, peat, lignite and paper mill waste which, to obtain the activated carbon, is reacted with an inorganic chemical compound to degrade or dehydrate the organic molecules during carbonization or calcination, while the latter type of activated carbon is commonly derived from coconut shells, coal, peat and petroleum residues which, to obtain the so-called "activated-type" carbon, is first carbonized and then oxidized with air at low temperature, or steam, carbon dioxide, or flue gas at high temperature. Carbons intended to be covered within the scope of this invention have the following properties: stable pore diameters of 15–20 A and total surface area (Langmuir method) in the range from 400–1500 m$^2$/g, preferably from 900–1200 m$^2$/g. Illustrative activated carbons, available from Calgon Corp., Pittsburgh, Pa. are types OL; PCB- and BPL-carbons. Typical of other properties of suitable adsorbent carbons are those of OL-carbon:

|  | Range |
| --- | --- |
| Apparent Bulk Density (ABD) | 0.48 (28.1 #/ft$^3$) |
| Particle Density (Hg Displ.) | 0.75 g/cc |
| Real Density (He Disl.) | 2.2 g/cc |
| Pore Volume | 0.54 cc/g |
| Voids in Dense Packed Column | 40% |
| Spec. Heat at 100° C. | 0.25 |
| Mesh Size U.S. Sieve Series | 20 × 50 |
| Iodine No. (min.) | 1000 |

Other objectives and embodiments of the invention encompass details about feed mixtures, adsorbents, desorbent material and operating conditions, all of which are hereinafter disclosed in the following discussion of each of the facets of the present invention.

DESCRIPTION OF THE INVENTION

The adsorbents used in the process of this invention can be better understood by brief reference to certain adsorbent properties which are necessary to the successful operation of a selective adsorption process. It will be recognized that improvements in any of these adsorbent characteristics will result in an improved separation process. Among such characteristics are: adsorptive capacity for some volume of an extract component per volume of adsorbent, the selective adsorption of an extract component with respect to a raffinate component and the desorbent material, sufficiently fast rates of adsorption and desorption of the extract component to and from the adsorbent; and, in instances where the components of the feed mixture are very reactive, little or no catalytic activity for undesired reactions such as polymerization and isomerization.

Feed mixtures to be used in the process of this invention include tall oil pitch which contains about 20–40% (wt.) sterols, primarily $\beta$-sitosterol, but also $\alpha$-sitosterol, $\beta$-sitostanol, campesterol, campestanol and stigmasterol. Impurities are: triterpene alcohols, fatty alcohols, diterpene aldehydes and polymeric materials. Also, wool fats are a feed source, particularly, of cholesterol, for separation by this invention. Other feeds may comprise more concentrated sterol from other processes, such as extracting adsorption, etc. The separation disclosed herein is a class-type separation, i.e., the sterols are selectively adsorbed on the carbon molecular sieve as a class in preference to the other constituents of the feed. To illustrate the type of structures which are adsorbed by the carbon sieves of the invention, the molecular structure of just two of the possible sterols which will be selectively adsorbed, $\beta$-sitosterol and cholesterol, are set forth below with the basic or general structural formula for steroids:

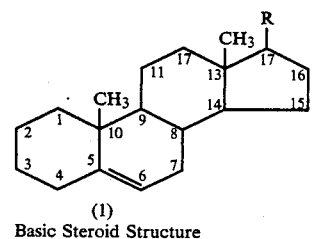

(1)
Basic Steroid Structure

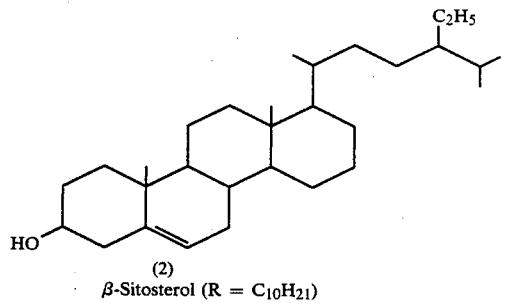

(2)
$\beta$-Sitosterol (R = C$_{10}$H$_{21}$)

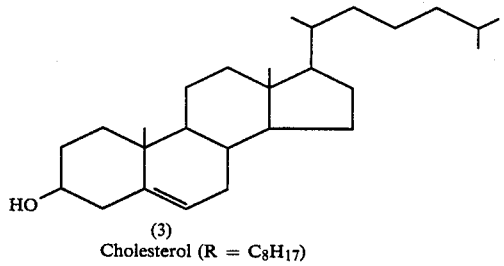

(3)
Cholesterol (R = C$_8$H$_{17}$)

To separate the sterols from a feed mixture containing at least one sterol, the feed mixture is contacted with the carbon absorbent; the sterol is more selectively adsorbed and retained by the adsorbent while the other feed constituents are relatively lesss from the intersitial adsorbed and are removed first by the desorbent void spaces between the particles of adosrbent and then the adsorbed sterols are eluted from the surface of the adsorbent.

The more selectively adsorbed feed components are commonly referred to as the extract component of the feed mixture, while the less selectively adsorbed component is referred to as the raffinate components. Fluid streams leaving the adsorbent comprising extract components and comprising raffinate components are referred to, respectively, as the extract stream and the raffinate stream. Thus, the raffinate stream will contain as a raffinate component the feed mixture components other than the more selectively adsorbed components and the extract stream will contain the more selectively adsorbed components as the extract component.

Although it is possible by the process of this invention to produce high purity, (mixed) sterol products at high recoveries, small amounts of a raffinate component can appear in the extract stream, and, likewise, small amounts of an extract component can appear in the raffinate stream. The extract and raffinate streams then are further distinguished from each other and from the feed mixture by the ratio of the concentrations of an extract component and a specific raffinate component, both appearing in the particular stream. The concentration of the more selectively adsorbed sterols will be highest in the extract stream, next highest in the feed mixture, and lowest in the raffinate stream. Likewise, the concentration of the less selectively adsorbed components will be highest in the raffinate stream, next highest in the feed mixture, and the lowest in the extract stream.

The adsorbent can be contained in one or more chambers where, through programmed flow into and out of the chambers, separation of the sterols is effected. The adsorbent will preferably be contacted with a desorbent material which is capable of displacing the sterols from the adsorbent. The resultant extract stream comprising the sterols and desorbent material may be subjected to a separation step, e.g. fractionation, so as to obtain the sterols in highly pure form.

An adsorbent which may be employed by this invention comprises an activated carbon (made by steam treatment of bituminous coal). A particularly suitable activated carbon comprises high temperature steam activated bituminous coal. It is in a granular form of from about 20–50 mesh size and has an ash content of 8 wt. %.

The adsorbent may be employed in the form of a dense compact fixed bed which is alternately contacted with the feed mixture and desorbent materials. In the simplest embodiment of the invention, the adsorbent is employed in the form of a single static bed in which case the process is only semi-continuous. In another embodiment, a set of two or more static beds may be employed in fixed bed contacting with appropriate valving so that the feed mixture is passed through one or more adsorbent beds while the desorbent materials can be passed through one or more of the other beds in the set. The flow of feed mixture and desorbent materials may be either up or down through the desorbent. Any of the conventional apparatus employed in static bed fluid-solid contacting may be used.

Countercurrent moving-bed or simulated moving-bed countercurrent flow systems, however, have a much greater separation efficiency than fixed adsorption bed systems and are, therefore, preferred for use in our separation process. In the moving-bed or simulated moving-bed processes, the adsorption and desorption operations are continuously taking place which allows both continuous production of an extract and a raffinate stream and the continual use of feed and desorbent streams. One preferred embodiment of this process utilizes what is known in the art as the simulated moving-bed countercurrent flow system. The operating principles and sequence of such a flow system are described in U.S. Pat. No. 2,985,589 incorporated herein by reference. In such a system, it is the progressive movement of multiple liquid access points down an adsorbent chamber that simulates the upward movement of adsorbent contained in the chamber. Only four of the access lines are active at any one time; the feed input stream, desorbent inlet stream, raffinate outlet stream, and extract outlet stream access lines. Coincident with this simulated upward movement of the solid adsorbent is the movement of the liquid occupying the void volume of the packed bed of adsorbent. So that countercurrent contact is maintained, a liquid flow down the adsorbent chamber may be provided by a pump. As an active liquid access point moves through a cycle, that is, from the top of the chamber to the bottom, the chamber circulation pump moves through different zones which require different flow rates. A programmed flow controller may be provided to set and regulate these flow rates.

The active liquid access points effectively divide the adsorbent chamber into separate zones, each of which has a different function. In this embodiment of the process, it is generally necessary that three separate operational zones be present in order for the process to take place, although in some instances an optional fourth zone may be used.

The adsorption zone, zone 1, is defined as the adsorbent located between the feed inlet stream and the raffinate outlet stream. In this zone, the feedstock contacts the adsorbent, an extract component is adsorbed, and a raffinate stream is withdrawn. Since the general flow through zone 1 is from the feed stream, which passes into the zone, to the raffinate stream which passes out of the zone, the flow in this zone is considered to be in a downstream direction when proceeding from the feed inlet to the raffinate outlet streams.

Immediately upstream with respect to fluid flow in zone 1 is the purification zone, zone 2. The purification zone is defined as the adsorbent between the extract outlet stream and the feed inlet stream. The basic operations taking place in zone 2 are the displacement from the non-selective void volume of the adsorbent of any raffinate material carried into zone 2 by the shifting of adsorbent into this zone and the desorption of any raffinate material adsorbed within the selective pore volume of the adsorbent or adsorbed on the surfaces of the adsorbent particles. Purification is achieved by passing a portion of extract stream material leaving zone 3 into zone 2 at zone 2's upstream boundary, the extract outlet stream, to effect the displacement of raffinate material. The flow of material in zone 2 is in a downstream direction from the extract outlet stream to the feed inlet stream.

Immediately upstream of zone 2 with respect to the fluid flowing in zone 2 is the desorption zone or zone 3. The desorption zone is defined as the adsorbent between the desorbent inlet and the extract outlet stream. The function of the desorption zone is to allow a desorbent material which passes into this zone to displace the extract component which was adsorbed upon the adsorbent during a previous contact with feed in zone 1 in a prior cycle of operation. The flow of fluid in zone 3 is essentially in the same direction as that of zones 1 and 2.

In some instances, an optional buffer zone, zone 4, may be utilized. This zone, defined as the adsorbent between the raffinate outlet stream and the desorbent inlet stream, if used, is located immediately upstream with respect to the fluid flow to zone 3. Zone 4 could be utilized to conserve the amount of desorbent utilized in the desorption step since a portion of the raffinate stream which is removed from zone 1 can be passed into zone 4 to displace desorbent material present in that zone out of that zone into the desorption zone. Zone 4 will contain enough adsorbent so that the raffinate material present in the raffinate stream passing out of zone 1 and into zone 4 can be prevented from passing into zone 3 thereby contaminating extract stream removed from zone 3. In the instances in which the fourth operational zone is not utilized, the raffinate stream passed from zone 1 to zone 3 must be carefully monitored in order that the flow directly from zone 1 to zone 3 can be topped when there is an appreciable quantity of raffinate material present in the raffinate stream passing from zone 1 into zone 3 so that the extract outlet stream is not contaminated.

A cyclic advancement of the input and output streams through the fixed bed of adsorbent can be accomplished by utilizing a manifold system in which the valves in the manifold are operated in a sequential manner to effect the shifting of the input and output streams thereby allowing a flow of fluid with respect to solid adsorbent in a countercurrent manner. Another mode of operation which can effect the countercurrent flow of solid adsorbent with respect to fluid involves the use of a rotating disc valve in which the input and output streams are connected to the valve and the lines through which feed input, extract output, desorbent input and raffinate output streams pass are advanced in the same direction through the adsorbent bed. Both the manifold arrangement and disc valve are known in the art. Specifically, rotary disc valves which can be utilized in this operation can be found in U.S. Pat. Nos. 3,040,777 and 3,422,848, incorporated herein by reference. Both of the aforementioned patents disclose a rotary type connection valve in which the suitable advancement of the various input and output streams from fixed sources can be achieved without difficulty.

In many instances, one operational zone will contain a much larger quantity of adsorbent than some other operational zone. For instance, in some operations the buffer zone can contain a minor amount of adsorbent as compared to the adsorbent required for the adsorption and purification zones. It can also be seen that in instances in which desorbent is used which can easily desorb extract material from the desorbent that a relatively small amount of adsorbent will be needed in a desorption zone as compared to the adsorbent needed in the buffer zone or adsorption zone or purification zone or all of them. Since it is not required that the adsorbent be located in a single column, the use of multiple chambers or a series of columns is within the scope of the invention.

It is not necessary that all of the input or output streams be simultaneously used, and in fact, in many instances some of the streams can be shut off while others effect an input or output of material. The apparatus which can be utilized to effect the process of this invention can also contain a series of individual beds connected by connecting conduits upon which are placed input or output taps to which the various input or output streams can be attached and alternately and periodically shifted to effect continuous operation. In some instances, the connecting conduits can be connected to transfer taps which during the normal operations do not function as a conduit through which material passes into or out of the process.

References can be made to the aforesaid D. B. Broughton U.S. Pat. No. 2,985,589, and to a paper entitled, "Continuous Adsorptive Processing—A New Separation Technique" by D. B. Broughton presented at the 34th Annual Meeting of the Society of Chemical Engineers at Tokyo, Japan, on Apr. 2, 1969, incorporated herein by reference, for further explanation of the simulated moving-bed countercurrent process flow scheme.

Adsorption and desorption conditions for adsorptive separation processes can generally be either in the liquid or vapor phase or both. Preferred adsorption conditions for the process of this invention will include temperatures within the range of from about 20° C. to about 230° C. and will include pressures in the range from about atmospheric to about 500 psig. Pressures higher than about 500 psig do not appear to effect the selectivity to a measurable amount and additionally would increase the cost of the process. Desorption conditions for the process of the invention shall generally include the same range of temperatures and pressures as described for adsorption operations. The desorption of the selectively adsorbed sterols could also be effected at subatmospheric pressures or elevated temperatures or both or by vacuum purging of the adsorbent to remove the sterols, but this process is not directed to these desorption methods. The desorbent material relied upon must be judiciously selected to satisfy several criteria. First, the desorbent material must displace the adsorbed sterols from the adsorbent with reasonable mass flow rates without itself being so strongly adsorbed as to unduly prevent the sterols from displacing the desorbent material in a following adsorption cycle. Secondly, desorbent materials must be compatible with the particular adsorbent and the particular feed mixture. More specifically, they must not reduce or destroy the critical selectivity of the adsorbent for the sterols with respect to the non-adsorbed components. The preferred desorbent material for use in the process of this invention is chlorobenzene, although others of equal or greater strength may also be useful. In the former category are tetralin; chlorotoluene; anisol and benzyl alcohol. A stronger desorbent is 1-methylnaphthalene.

A dynamic testing apparatus may be employed to test various adsorbents with a particular feed mixture and desorbent material to measure the adsorbent characteristics of adsorptive capacity, selectivity and exchange rate. The apparatus consists of an adsorbent chamber of approximately 70 cc volume having inlet and outlet portions at opposite ends of the chamber. The chamber is contained within a temperature control means and, in addition, pressure control equipment is used to operate the chamber at a constant predetermined pressure. Chromatographic analysis equipment can be attached to the outlet line of the chamber and used to detect qualitatively or determine quantitatively one or more components in the effluent stream leaving the adsorbent chamber. A pulse test, performed using this apparatus and the following general procedure, is used to determine selectivities and other data for various adsorbent systems. The adsorbent is filled to equilibrium with a particular desorbent material by passing the desorbent material through the adsorbent chamber. At a convenient time, a pulse of feed containing known concentrations of a non-adsorbed light fraction and of an mixture of sterols and heavy fraction, all diluted in desorbent, is injected for a duration of several minutes. Desorbent flow is resumes, and the feed components are eluted as in a liquid-solid chromatographic operation. The effluent is collected in fractions and analyzed using chromatographic equipment and traces of the envelopes of corresponding component peaks developed.

From information derived from the test, adsorbent performance can be rated in terms of retention volume for an extract or a raffinate component, selectivity for one component with respect to the other, and the rate of desorption of an extract component by the desorbent. The retention volume of an extract or a raffinate component may be characterized by the distance between the center of the peak envelope of an extract or a raffinate component and the peak envelope of the tracer component or some other known reference point. It is expressed in terms of the volume in cubic centimeters of desorbent pumped during this time interval represented by the distance between the peak envelopes. Selectivity, ($\beta$), for an extract component with respect to a raffinate component may be characterized by the ratio of the distance (expressed in cc's) between the center of the extract component peak envelope and the tracer peak envelope (or other reference point) to the corresponding distance between the center of the raffinate component peak envelope and the tracer peak envelope. The rate of exchange of an extract component with the desorbent can generally be characterized by the width of the peak envelopes at half intensity. The narrower the peak width the faster the desorption rate.

Where selectivity of two components approaches 1.0 there is no preferential adsorption of one component by the adsorbent with respect to the other; they are both adsorbed (or non-adsorbed) to about the same degree with respect to each other. As the ($\beta$) becomes less than or greater than 1.0, there is a preferential adsorption by the adsorbent for one component with respect to the other. When comparing the selectivity by the adsorbent of one component C over component D, a ($\beta$) larger than 1.0 indicates preferential adsorption of component C within the adsorbent. A ($\beta$) less than 1.0 would indicate that component D is preferentially adsorbed leaving an unadsorbed phase richer in component C and an adsorbed phase richer in component D. Ideally, desorbent materials should have a selectivity equal to about 1 or slightly less than 1 with respect to all extract components so that all of the extract components can be desorbed as a class with reasonable flow rates of desorbent material and so that extract components can displace desorbent material in a subsequent adsorption step. While separation of an extract component from a raffinate component is theoretically possible when the selectivity of the adsorbent for the extract component with respect to the raffinate component is greater than 1.0, it is preferred that such selectivity be greater than 2.0. Like relative volatility, the higher the selectivity the easier the separation is to perform. Higher selectivities permit a smaller amount of adsorbent to be used. The rate of exchange relates directly to the amount of desorbent material that must be employed in the process to recover the extract component from the adsorbent; faster rates of exchange reduce the amount of desorbent material needed to remove the extract component and, therefore, permit a reduction in the operating cost of the process. With faster rates of exchange, less desorbent material has to be pumped through the process and separated from the extract stream for reuse in the process.

It is also necessary that the adsorbent possess little or no catalytic activity toward any reaction such as polymerization or isomerization of any of the feed components. Such activity might effect adsorbent capacity, stability, selectivity or product yields, or all of these. Tall oil pitch or other tall oil feeds may contain impurities which can polymerize within the pore structure of the adsorbent and deactivate the adsorbent. Among the possible impurities which are reactive is squalene, found in solvent extracted tall oil. We have avoided this by employing an activated carbon adsorbent, which is stable to the acid impurities contained in the feed which deactivate other adsorbents such as alumina, florisil and silica.

To further evaluate promising adsorbent systems and to translate this type of data into a practical separation process, actual testing of the best system in a continuous countercurrent liquid-solid contacting device would be ideal. The general operating principles of such a device have been previously described and are found in Broughton U.S. Pat. No. 2,985,589 and a specific laboratory-size apparatus utilizing these principles is described in deRosset et al. U.S. Pat. 3,706,812. The equipment comprises multiple adsorbent beds with a number of access lines attached to distributors within the beds and terminating at a rotary distributing valve. At a given valve position, feed and desorbent are being introduced through two of the lines and raffinate and extract are withdrawn through two more. All remaining access lines are inactive and when the position of the distributing valve is advanced by one index, all active positions will be advanced by one bed. This simulates a condition in which the adsorbent physically moves in a direction countercurrent to the liquid flow. Additional details on adsorbent testing and evaluation may be found in the paper "Separation of $C_8$ Aromatics by Adsorption" by A. J. deRosset, R. W. Neuzil, A. J. Korous, and D. H. Rosback presented at the American Chemical Society, Los Angeles, Calif., Mar. 28 to Apr. 2, 1971. All of the above references are incorporated herein by reference.

ILLUSTRATIVE EXAMPLE AND BRIEF DESCRIPTION OF THE DRAWINGS

The following example is of pulse test results obtained from the above described pulse test apparatus. The adsorbent column was helical with capillary controlled pressure (200 psi). Feed pulses were 5 ml each. The flow was through the column at a rate of 1.1 ml/min. The adsorbent chamber was packed with adsorbent comprising activated carbon given an oxidation treatment as described above (OL-Calgon Corp). The adsorbent comprised hard granules of from 20-50 mesh size having a substantial percentage of the pore sizes in the range from 15-20 Å, a calculated pore diameter of 15.6 Å, an apparent bulk density (ABD) of 0.48 gm/ml, a pore volume of 0.54 ml/g and a surface area of 1340 $m^2/g$. The desorbent selected was chlorobenzene.

FIG. 2 is a trace of the chromatographic separation of a feed having a higher concentration of sterols as described in Example III.

EXAMPLE I

Figure 1:
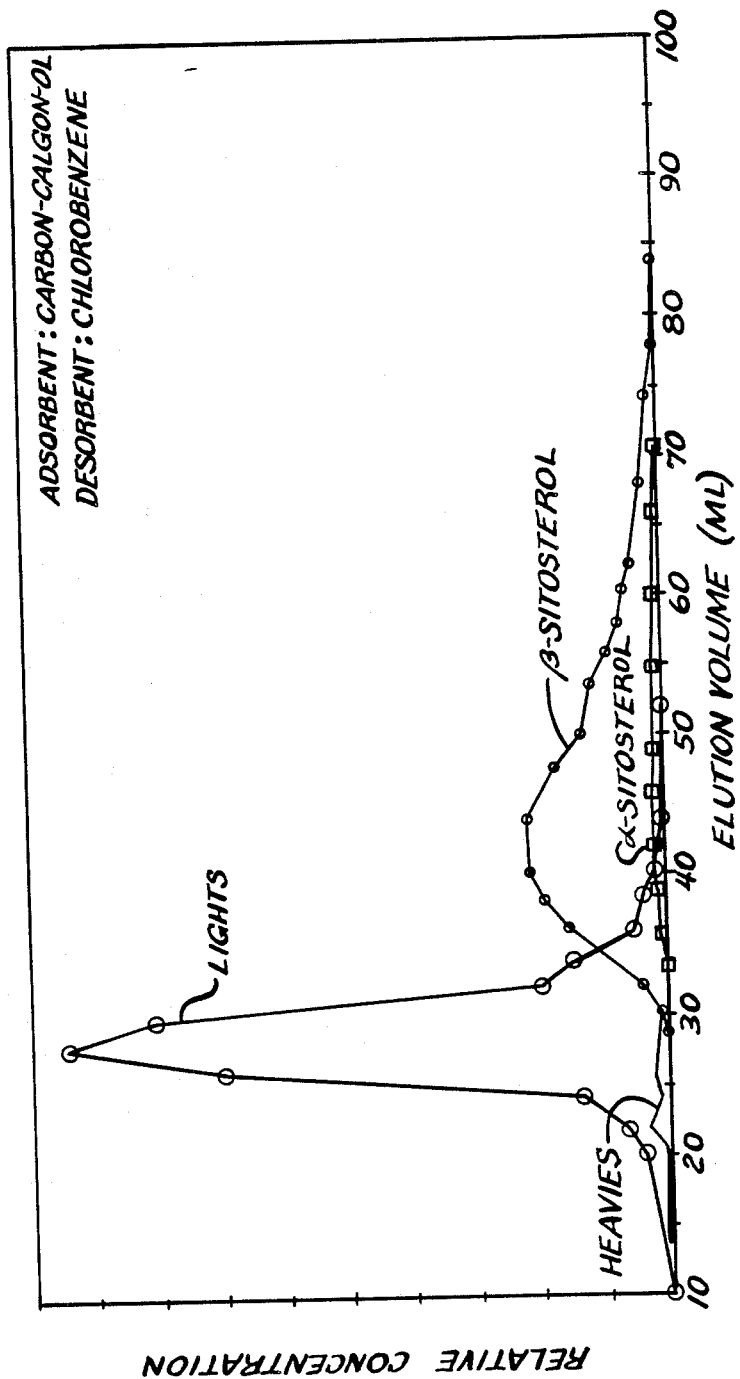
FIG. 1 is a trace of the chromatographic separation described in Example I.

In this example, sterols were separated from tall oil pitch using chlorobenzene as the desorbent, a temperature of 120° C. and pressure sufficient to maintain liquid phase. The adsorbent was Calgon OL carbon. The feed contained about 37% (wt.) sterols, primarily $\beta$-sitosterol. The balance of the feed was fatty acid ethanolamides, resin acids, triterpene alcohols, fatty alcohols, diterpene aldehydes and some polymeric materials. The net retention volume for the fractions and the selectivity ($\beta$) is listed in the following Table 1.

TABLE 1

|  | Sterols | Lights |
|---|---|---|
| Net Retention Volume | 17.7 | 2.9 |
| $\beta$ Sterols/Lights |  | 6.1 |

The results are shown in FIG. 1 of the drawings. FIG. 1 shows separation of the sterols (labelled $\alpha$- and $\beta$-sitosterol) from nonadsorbed fractions of the feed, labelled lights, which include fatty acid ethanol amides, resin acids and fatty neutrals and heavies, other than sterols, which include the polymeric materials referred to earlier.

EXAMPLE II

A separation was performed in a pilot plant using the principles and equipment disclosed in Broughton U.S. Pat. No. 2,985,589 and described in detail in de Rossett Patent 3,706,812 with a feed which analyzed 24.8% sterols (13.8% $\beta$-sitosterol) with the same carbon adsorbent as Example I. The temperature was 150° C. The desorbent was monochlorobenzene. Sterol purity was 77.6% with 89% recovery (51% $\beta$-sitosterol at 99+% recovery) in a column filled with 515 gm of adsorbent. The feed rate was 23 cc/hr. and cycle time was 1 hour.

EXAMPLE III

Another pulse test similar to Example I was run to separate sterols from a feed mixture comprising a mixture of extracts from a number of separation runs like Example II. The feed composition was 84.4% sterols (54.4% $\beta$-sitosterol). Sterols (as a class) and intermediates, which included dehydrated sterols and other non-sterol impurities such as resin acid derivatives were removed in the extract stream and while the bulk of the lights, comprising fatty alcohols, triterpene alcohols, diterpene aldehydes and polymeric materials are primarily removed in the raffinate stream. The temperature was 160° C. and the desorbent was chlorobenzene. The results are shown in FIG. 2 and the following Table 2.

TABLE 2

|  | Sterols | Intermediates | Lights |
|---|---|---|---|
| Net Retention Vol | 11.7 | 20.4 | 5.0 |
| $\beta$ | 1.0 | 0.57 | 2.34 |

What is claimed is:

1. A process for separating sterols from a tall oil feed mixture, which process comprises contacting at adsorption conditions said mixture with an adsorbent comprising an activated-type carbon sieve, selectively adsorbing said sterols onto said adsorbent, and treating said adsorbent containing said sterols with a desorbent material comprising an aromatic liquid hydrocarbon to desorb said sterols therefrom as a fluid extract stream.

2. The process of claim 1 further characterized in that said desorbent comprises chlorobenzene.

3. The process of claim 2 wherein said sterols comprise $\beta$-sitosterol.

4. The process of claim 2 wherein said sterols comprise cholesterol.

5. The process of claim 1 further characterized in that said adsorption conditions include a temperature within the range of from about 20° C. to about 30° C. and at as pressure within the range of from about atmospheric about 500 psig.

6. The process of claim 1 wherein said carbon sieve is activated carbon.

7. The process of claim 1 wherein the pore diameter of said carbon sieve is from 15-20 Å and the surface area is in the range of 400-1500 $m^2/g$.

8. The process of claim 1 wherein the surface area of said adsorbent is in the range of from 900-1200 Å.

9. A process for separating sterols from a tall oil feed mixture which process comprises contacting at adsorption conditions said mixture with an adsorbent comprising activated carbon which process comprises the steps of:
   (a) maintaining net fluid flow through a column of said adsorbent in a single direction, which column contains at least three zones having separate operational functions occurring therein and being serially interconnected with the terminal zones of said column connected to provide a continuous connection of said zones;
   (b) maintaining an adsorption zone in said column, said zone defined by the adsorbent located between a feed inlet stream at an upstream boundary of said zone and a raffinate outlet stream at a downstream boundary of said zone;
   (c) maintaining a purification zone immediately upstream from said adsorption zone, said purification zone defined by the adsorbent located between an extract outlet stream at an upstream boundary of said purification zone and said feed inlet stream at a downstream boundary of said purification zone;
   (d) maintaining a desorption zone immediately upstream from said purification zone, said desorption zone defined by the adsorbent located between a desorbent inlet stream at an upstream boundary of said zone and said extract outlet stream at a downstream boundary of said zone;
   (e) passing said feed stream into said adsorption zone at adsorption conditions to effect the selective adsorption of said sterols by said adsorbent in said adsorption zone and withdrawing a raffinate outlet stream from said adsorption zone;
   (f) passing a desorbent material into said desorption zone at desorption conditions to effect the displacement of said sterols from the adsorbent in said desorption zone, said desorbent material comprising chlorobenzene;
   (g) withdrawing an extract stream comprising said sterols and desorbent material from said desorption zone;
   (h) periodically advancing through said column of adsorbent in a downstream direction with respect to fluid flow in said adsorption zone the feed inlet stream, raffinate outlet stream, desorbent inlet stream, and extract outlet stream to effect the shifting of zones through said adsorbent and the production of extract outlet and raffinate outlet streams.

10. The process of claim 9 further characterized in that it includes the step of maintaining a buffer zone immediately upstream from said desorption zone, said buffer zone defined as the adsorbent located between the desorbent input stream at a downstream boundary of said buffer zone and a raffinate output stream at an upstream boundary of said buffer zone.

11. The process of claim 9 further characterized in that said adsorption conditions and desorption conditions include a temperature within the range of from about 20° C. to about 230° C. and a pressure within the range of from about atmospheric to about 500 psig.

12. The process of claim 9 wherein said sterols comprise β-sitosterol.

13. The process of claim 9 wherein said sterols comprise cholesterol.

14. The process of claim 9 wherein the pore diameter of said activated carbon is from 15–20 Å and the surface area is from 400–1500 m$^2$/g.

* * * * *